United States Patent [19]

Bernier et al.

[11] Patent Number: 5,116,746
[45] Date of Patent: May 26, 1992

[54] CELLULASE-FREE ENDO-XYLANASE ENZYME OF USE IN PULP DELIGNIFICATION

[75] Inventors: Roger L. Bernier, Mississauga; Dieter Kluepfel, Montreal; Rolf Morosoli, Ville St-Laurent; Francois Shareck, Dollard-des-Ormeaux, all of Canada

[73] Assignee: Institut Armand Frappier, Quebec, Canada

[21] Appl. No.: 764,083

[22] Filed: Sep. 23, 1991

Related U.S. Application Data

[63] Continuation of Ser. No. 164,472, Mar. 4, 1988, abandoned.

[51] Int. Cl.⁵ .......................... D21C 3/00; C12N 1/21; C12N 15/52; C12N 15/76
[52] U.S. Cl. ............................... 435/172.3; 435/69.1; 435/71.1; 435/91; 435/169; 435/172.1; 435/200; 435/252.3; 435/252.35; 435/320.1; 435/886; 536/27; 162/1; 935/6; 935/9; 935/14; 935/22; 935/59; 935/60; 935/64; 935/72
[58] Field of Search .................. 162/1; 435/69.1, 71.1, 435/91, 169, 172.1, 172.3, 200, 252.3, 252.35, 320.1, 886; 536/27; 935/6, 9, 14, 22, 29, 54, 60, 64, 72, 75

[56] References Cited

FOREIGN PATENT DOCUMENTS 2557894 12/1985 France .

OTHER PUBLICATIONS

Bernier, R., Driquez, H. and Desrochers, M., Gene; 26, 59 (1983).
Iwasaki, A., Kishida, H. and Okanishi, M., J. Antibiotics: 39(7),985 (1986).
Viikari, L., Ranua, M., Kantelinen, A., Linko, M. and Sundquist, J., Proceedings of the International Symposium on Wood & Pulping Chemistry, Paris (1987).
Mondou, F., Shareck, F., Morosoli, R. and Kluepfel, D., Gene: 49(3), 323 (1986).
Chauvet, J-M., Comtat, J. and Noe, P., Proceedings of the International Symposium on Wood & Pulping Chemistry, Paris (1987).

Primary Examiner—Richard C. Peet
Attorney, Agent, or Firm—Cushman, Darby & Cushman

[57] ABSTRACT

A method of treating lignocellulosic material with a cellulase-free endo-xylanase for delignification, brightening and viscosity improvement. The endo-xylanase is obtained by the overexpression of the xylanase gene using a cellulase-negative recombinant microorganism of the genus Streptomyces. The recombinant microorganism is produced in a homologous cloning system in which the xylanase gene is inserted into a vector plasmid to provide the hybrid plasmid that is introduced into a host cellulase-negative mutant strain and said xylanase gene, said vector plasmid and said host mutant strain are obtained from microorganisms of the genus Streptomyces.

27 Claims, No Drawings

CELLULASE-FREE ENDO-XYLANASE ENZYME OF USE IN PULP DELIGNIFICATION

This is a continuation of application Ser. No. 07/164,472, filed on Mar. 4, 1988, which was abandoned upon the filing hereof.

FIELD OF THE INVENTION

The present invention relates to genes coding for hydrolase enzymes, specifically endo-xylanases, hybrid plasmids containing the related genes, cellulase-negative host microorganisms of the species *Streptomyces lividans* that are transformed with the plasmids, cellulase-negative recombinant microorganisms that overexpress the enzymes and to the enzymatic treatment of lignocellulosic material with the aforementioned enzymes resulting in delignification, brightening and viscosity improvement.

BACKGROUND OF THE INVENTION

As reviewed by Joseleau and Gancet (Svensk Papperstidning; R123 (1981)), the cohesion of the plant cell wall is primarily due to the presence of its principal components: a crystalline polymer, cellulose, and a three-dimensional macromolecule, lignin, comprising a lignocellulosic material. These components are embedded in a matrix of pectic and hemicellulotic polysaccharides of various nature. It is generally accepted that the relations that exist between these different polymers are established through linkages of different chemical nature. For instance, blocks of lignin are associated through hemicellulose chains. The hemicellulose, another major component of lignocellulosic material, consists largely of 4-O-methylglucuronoxylan, which includes the $\beta$-1,4-linked polymer of D-xylose, and herein referred to as xylan. Generally, hardwood pulps contain larger amounts of xylan than do softwood pulps. Such xylan can be enzymatically hydrolyzed to xylose by an endo-xylanase, $\beta$-1,4-D-xylan xylanohydrolase, denoted EC 3.2.1.8, and a xylosidase, $\beta$-1,4-D-xylohydrolase, denoted EC 3.2.1.37, as discussed by Bernier et al. (Biotechnol. Letters; 7 (11), 797(1985)).

Surprisingly, we have now found that the partial or total digestion of xylan contained in lignocellulosic materials through the use of endo-xylanases, as hereinafter described, provides an attractive alternative to the totally mechanical and/or chemical process for the production of pulps having improved pulp properties such as brightness index. We have found that the production of enzymes suitable for providing improved pulp properties through enzymatic treatment, which production is often quite low in naturally occurring microorganisms, has to be enhanced, in order to be commercially feasible. Further, because release of lignin by hemicellulose cleavage has to be specific in order to prevent the deterioration of certain pulp qualities, e.g. viscosity, that arise due to cellulose hydrolysis, a substantially cellulase-free xylanase mixture has to be used.

Thus, by the molecular cloning and modification of the expression levels of genes coding for endo-xylanase, improved production of such enzymes that are substantially cellulase-free has been attained, and found to be of value for pulp treatment.

The techniques of recombinant genetic technology are known and usually comprise, at their simplest, the steps of obtaining from a donor cell the DNA fragment or gene coding for a desired metabolite or enzyme, cleaving a suitable vector plasmid to provide an insertion site wherein the aforesaid DNA fragment may be inserted into the vector plasmid, inserting the aforesaid DNA into the vector to form a hybrid plasmid, genetically modifying a host bacterium by introducing the hybrid plasmid carrying the aforesaid DNA fragment into the host and culturing the resulting genetically modified (recombinant) bacterium to cause it to produce the desired metabolite.

Molecular cloning of the gene coding for xylanase production has been accomplished in a heterologous system (Bernier, R. et al., Gene; 26, 59 (1983)), wherein the donor strain for the chromosomal DNA was a microorganism of the species *Bacillus subtilis* and the required DNA fragment (xylnase gene) was cloned and expressed in *Escherichia coli* as host. The resultant recombinant *Escherichia coli* was cellulase-negative but the disadvantages associated with such systems include: low levels of protein or enzyme production, gene instability and limited extracellular secretion of the enzyme.

Iwasaki et al. (J. Antibiotics; 39(7), 985 (1986)) reports the molecular cloning of a xylanase gene from the donor strain *Streptomyces* sp. No. 36a in a homologous system using *Streptomyces lividans* TK21 as host. The vector plasmid into which aforesaid gene is inserted is pIJ702. The transformants harboring the newly constructed plasmids produce about 10 to 70 times higher levels of extracellular xylanase than that of the donor strain. However, there is no indication of having removed the cellulase activity in the transformants and it is known that under natural circumstances microorganisms of the species *Streptomyces lividans* produce cellulase.

As a means for the production of an enzymic protein which: 1) exhibits a hydrolase activity, mainly an endo-$\beta$-D-xylan hydrolase activity; 2) is cellulase-free 3) is overproduced and present in the supernatant during the growth of a recombinant *Streptomyces lividans* microorganism (extracellularly secreted) and 4) is soluble in water; the present invention hereinafter defined provides a gene system coding for such an enzyme.

In the treatment of pulps with cellulase-free xylanase that is present in the supernatant in which a suitable microorganism is grown, the cleavage of the hemicellulose will liberate residual lignin present after pulping, and facilitate its partial removal. The removal of lignin is normally associated with a decrease in the Kappa number of the pulp and may be accompanied by an increase in the brightness. A third pulp parameter, viscosity, is normally considered to be a reflection of the extent of cellulose degradation. Viscosity is affected by the degree of crystallinity and the nature of the intermolecular bonding.

French Patent Application No. 2,557,894 (published 1985) discloses a process for treating a hardwood bleached sulphite chemical paper pulp with an enzymatic solution containing xylanase. Particularly large amounts of enzyme are required for the treatment of the bleached pulp in order to impart the effect of relaxation of the pulp fiber structure, which results in the benefit of reducing the amount of subsequent refining required for papermaking. Further, the xylanase secreted by the basidiomycete mushroom *Sporotrichum dimorphosporum* for use in the reduction of refining, was not cellulase-free and the detrimental cellulase activity was found to be suppressed by the addition of mercuric chloride in the process. However, due to the known toxic and other harmful effects associated with exposure to mercury-containing compounds, their use in removing or inactivating the cellulase enzymes constitutes a distinct disadvantage.

The application of xylanase on hardwood and softwood Kraft pulp for the purpose of brightness improvement and Kappa number reduction upon subsequent bleaching is discussed by Viikari et al. (Proceedings of the International Symposium On Wood and Pulping Chemistry, Paris (1987)). The xylanases are obtained by fermentation of a strain of fungus of the species *Aspergillus awamori* or by fermentation of bacterial strains of *Streptomyces olivochromogenes* or *Bacillus subtilis*. The xylanases exhibit both endo-xylanase and xylosidase activities except the xylanase from the latter bacteria that is xylosidase-free. The enzyme preparations contain traces of cellulase activity. A small brightness increase is observed with either the hardwood or softwood pulp after peroxide delignification following the enzymatic treatment of from 1.0 to 3.4 brightness points, as compared to the brightness achieved in appropriate control experiments, depending on the source of xylanase. The Kappa number reduction for peroxide delignification following enzymatic treatment, as compared to appropriate control experiments, is from 3% to 16% for softwood pulp and from 9% to 22% for hardwood pulp. In many instances, the resulting pulp viscosities were preserved or only slightly lower. There is no indication as to the effect of the enzyme treatment alone on these pulp properties. It is evident, however, that xylanase preparations from different microorganisms impart different effects on pulp properties.

Chauvet et al. (Proceedings of The International Symposium On Wood And Pulping Chemistry, Paris, p. 325, (1987)) report on the use of a xylanase preparation obtained from the basidomycete mushroom *Sporotrichum dimorphosporum* for use as a pretreatment for conventional chemical pulp bleaching. The crude enzymatic complex is treated in a way that inactivates all polysaccharidase except xylanase activities. The pulp pretreatment comprises an enzymatic treatment followed by washing and subsequent aqueous acid soaking that results in up to a 14% Kappa number reduction for the hardwood sample. The pulp strength is not modified by xylanase in this example.

SUMMARY OF THE INVENTION

It is a principal object of the present invention to provide a method of treating lignocellulosic material, preferably a chemical pulp, with an endo-xylanase that is substantially cellulase-free for the purpose of hydrolysis of the β-1,4-D-xylosidic linkage in order to improve pulp properties.

It is a further object of the present invention to provide a recombinant microorganism of the genus Streptomyces that is capable of being cultured for the extracellular production of cellulase-free endo-xylanase.

Accordingly, in one aspect the invention provides a method of hydrolyzing the β-1,4-D-xylosidic linkage within a lignocellulosic material having xylanase hydrolyzable β-1,4-D-xylosidic linkages, said method comprising subjecting said material to said hydrolysis by a substantially cellulase-free xylanase obtained from the recombinant microorganism produced by the introduction of a hybrid plasmid into a host microorganism mutant strain of the genus Streptomyces, said strain characterized by it having cellulase-negative activity, said hybrid plasmid being constructed by the insertion of the xylanase (xln) gene obtained from a xylanase (xln) gene-containing microorganism of the genus Streptomyces into a vector plasmid obtained from a microorganism of the genus Streptomyces. Preferably the xylanase is an endo-xylanase, also referred to as xylanase or β-1,4-D-xylan xylanohydrolase, designated EC 3.2.1.8, characterized as being substantially cellulase-free. By the term "substantially cellulase-free" is meant those systems which do not contain sufficient amount of cellulase to effect the unfavourable hydrolysis of glucosidic linkages. This hydrolysis clearly would be detrimental and unwanted in the treatment of lignocellulosic material for the purpose of improving pulp properties as in accordance with the method of the present invention herein defined. The amount of cellulase that may be tolerated depends on the particular objective in the practice of this invention. The endo-xylanase is secreted extracellularly into a culture medium of a recombinant microorganism in the presence of a suitable carbon source.

The xylanase hydrolyzable β-1,4-D-xylosidic linkage is within the xylan that is contained in the hemicellulose of the lignocellulosic material. The enzymatic degradation of the xylan by hydrolysis of the β-1,4-D-xylosidic linkages is partial and thus there is no drastic release of xylose and xylobiose. According to the present invention, the treatment of lignocellulosic material, preferably a chemical pulp, by xylanase that is cellulase-free results in delignification, brightening and viscosity improvement. Further, such treatment may provide more relaxed fibers resulting in improved performance of a subsequent treatment, such as swelling, beating, cooking or bleaching of the pulp.

In a further aspect, the invention provides a recombinant microorganism which contains a hybrid plasmid that carries a xln gene that codes for the production of xylanase, wherein said plasmid is capable of inducing the extracellular secretion of cellulase-free xylanase in a host microorganism into which said plasmid has been introduced, wherein said host microorganism is a mutant strain of the genus Streptomyces, said strain characterized by it having cellulase-negative activity. A host microorganism mutant strain characterized by it having cellulase-negative activity, as described herein the present invention, includes those mutant strains that may have also other enzyme-negative activities. Preferably the host microorganism is a mutant strain of the species *Streptomyces lividans*, said strain characterized by it having cellulase-negative activity. More preferably, the host microorganism is a double mutant strain of the genus Streptomyces, said strain characterized by it having also xylanase-negative activity. Yet more preferably the host microorganism is a double mutant strain of the species *Streptomyces lividans*, said strain characterized by it having also xylanase-negative activity. Still yet more preferably the host microorganism is the double mutant strain *Streptomyces lividans* 10-164 characterized by its cellulase-negative and xylanase-negative activities. In yet a further aspect, the invention provides the hybrid plasmid constructed by the insertion of a xylanase (xln) gene into a vector plasmid, wherein said gene and said vector plasmid are both obtained from microorganisms of the genus Streptomyces. Preferably, the xylanase (xln) gene and/or the vector plasmid are obtained from microorganisms of the species *Streptomyces lividans*. More preferably, the xylanase (xln) gene is obtained from the strain *Streptomyces lividans* 1326 and- /or the vector plasmid is pIJ702 obtained from the strain *Streptomyces lividans* 3131.

In a further aspect, the invention provides the recombinant microorganisms hereinabove defined of use in the production of the cellulase-free xylanase.

In yet a further aspect, the invention provides the host microorganisms and the hybrid plasmids hereinabove defined for use in the production of the recombinant microorganisms.

In still yet a further aspect, the invention provides a method for the production of a recombinant microorganism hereinabove defined, comprising the introduction of a hybrid plasmid hereinabove defined into a host microorganism hereinabove defined.

The hybrid plasmid may be introduced into the host microorganism by the technique of protoplast fusion or preferably by transduction or more preferably by transformation.

The xylanase (xln) gene is said to have been cloned upon its introduction into the host microorganism, hereinabove defined, thus providing a recombinant microorganism characterized by at least its cellulase-negative activity. The expression of the xln gene in the recombinant microorganism results in the production of cellulase-free xylanase.

DETAILED DESCRIPTION OF THE INVENTION

The recombinant microorganism of the present invention contains a hybrid plasmid that carries the xln gene that codes for the production of xylanase. The hybrid plasmid can be constructed by any conventional methods for the insertion of the required DNA fragment (xln gene) into a vector plasmid. Preferably, chromosomal DNA is extracted from *Streptomyces lividans* 1326, available from the National Collection of Industrial and Marine Bacteria Limited, Aberdeen, U.K. under Accession number NCIMB 40257, and partially digested with restriction enzyme Sau3A. The resulting fragments that include the required xylanase (xln) gene are collected by fractionation. A vector plasmid can be obtained from a microorganism of the genus Streptomyces. The vector plasmid pIJ702 is obtained from *Streptomyces lividans* 3131, a culture of which Streptomyces lividans 3131 carrying pIJ702 is on deposit at the American Type Culture Collection under Accession number ATCC 35287 digested with restriction enzyme BglII, ethanol precipitated and dephosphorylated. The hybrid plasmid is produced by the technique of ligation, wherein the partially digested chromosomal DNA fragments and dephosphorylated vector plasmid pIJ702 are treated with DNA ligase.

The recombinant microorganism is produced by the introduction of the hybrid plasmid into a host microorganism mutant strain of the genus Streptomyces, wherein said strain is characterized by it having β-1,4-D-glucan glucanohydrolase-negative (cellulase-negative) activity. The recombinant microorganism is produced by the conventional technique of functional complementation of a host xylanase-negative and cellulase-negative double mutant strain *Streptomyces lividans*, using the hybrid plasmid, as described by Kluepfel et al. (Gene; 49(3), 323 (1987)).

The host double mutant is produced by exposing a microorganism of the genus Streptomyces using an appropriate mutating agent. Preferably, the host double mutant *Streptomyces lividans* 10-164 is produced by exposing the strain *Streptomyces lividans* 1326 to N-methyl-N'-nitro-N-nitrosoguanidine. An endocellulase-negative mutant is selected by replicating the surviving colonies on a solid minimal medium containing some carboxymethyl-cellulose. Visualization of endocellulase activity is achieved by Congo Red staining according to Teather and Wood (Appl. Environ. Microbiol.; 43, 777, (1982)). The detection of a xylanase-negative mutant is carried out in the same manner substituting the carboxymethyl-cellulose by oat spelts xylan.

The host double mutant *Streptomyces lividans* 10-164 is transformed by the technique described by Chater et al. (Curr. Topics Microbiol. Immunol.: 97, 69 (1982)). Transformants were screened for xylanase-positive activity and two clones, designated *Streptomyces lividans* IAF18 and IAF30 were selected.

The extracellular xylanase produced by the recombinant strain *Streptomyces lividans* IAF18 was purified to homogeneity. The purified enzyme has an apparent $M_r$ of 43,000 daltons and pI of 5.2. This $M_r$ value corresponds exactly to the $M_r$ value of the native purified xylanase from *Streptomyces lividans* 1326 and the xylanase from the recombinant strain *Streptomyces lividans* IAF30 determined by a comparison of the xylanase analysis for culture supernatant concentrates by SDS-PAGE after staining with Coomassie Blue, and by autoradiogram of a Western blot probed with antixylanase antibodies combined with [$^{125}$I] protein A. These results confirmed the identity of these proteins and indicated that both clones had inserts coding at least for the complete structural gene. Also, the xylanase produced by *Streptomyces lividans* IAF18 showed no activity towards CM-cellulose and p-nitrophenyl β-D-xyloside. The enzyme degrades xylan, producing mainly xylobiose, a mixture of xylo-oligosaccharides and a small amount of xylose as end products (Morosoli et al., Biochem. J.: 239, 587 (1986)). The level of xylanase production in the original *Streptomyces lividans* is approximately 70 IU/ml of supernatant. After cloning, the level of production reaches approximately 380 IU/ml of supernatant.

The expression of the xylanase gene varies according to the source of carbon used in the culture medium. The xylanase is produced by *Streptomyces lividans* IAF18 in culture medium containing 1% of hay, wheat straw, corn stover or brewer's spent grains (BSG) as main carbon sources. Preferably, replacing completely the organic nitrogen sources in the culture medium with brewer's spent grains (BSG) improves the production of xylanase. More preferably, surfactants such as Tween 80 or olive oil are used in the culture medium with 1% BSG. Yet more preferably, the carbon source in the growth medium is xylan. *Streptomyces lividans* 1326 cultured in medium containing 2% xylan produces xylanase at a concentration of 28 IU/ml, whereas *Streptomyces lividans* IAF18 under said culture conditions produces xylanase at a concentration of 1600 IU/ml. Optimization of growth conditions increases this level up to 2,000 IU/ml.

Further, in accordance with the method of the present invention, an aqueous northern or southern hardwood or softwood pulp is treated with a cellulase-free xylanase. While it is preferred to employ a Kraft pulp, other chemically digested pulps may be used. The unbleached Kraft pulp is treated with endo-xylanase contained in the supernatant of a recombinant *Streptomyces lividans* clone at a concentration of enzyme ranging from about 1 to about 500 IU/ml and at a temperature of from about 20° C. to about 80° C., preferably about 50° C. Such supernatant is free of cellulases and therefore provides for a specific attack of the xylans. The consistency of the pulp is from about 0.1% to about 30%, based on the oven-dry weight of the pulp. A consistency of from about 2% to about 12% is preferred. The mixture can be agitated at various speeds with the use of various mixing devices. The pulp is subsequently treated in various ways depending upon the type of paper product desired. Preferably, the xylanase-treated pulp is subjected to alkali extraction in order to further improve the pulp properties, such as to achieve a higher brightness. Preferably the alkali extraction is performed at about 60° C. for about 10 to 60 minutes. Again, the pulp is subsequently treated in various ways depending upon the type of paper product desired.

In some instances, it is necessary to optionally include a pretreatment in order to prepare the pulp so that when the pulp is treated, the enzyme will be able to function in the manner described in the present invention.

The xylanase action can be inhibited by heating of the pulp solution to about 90° C. for the required amount of time. The enzyme solution can be purified and/or concentrated using fractionation and/or separation techniques known in the art.

With reference to Examples, methods for the construction of the hybrid plasmid, the production fo the recombinant microorganism, the extracellular secretion of xylanase and the treatment of lignocellulosic material with xylanase, will be explained.

EXAMPLE 1

Chromosomal DNA was extracted from *Streptomyces lividans* 66 (strain 1326) and partially digested with Sau3A. The resulting fragments were fractionated on a linear 10 to 40% sucrose gradient. The enriched fractions containing 4 to 10 kb fragments were pooled prior to ethanol precipitation. Vector plasmid pIJ702, obtained from *Streptomyces lividans* 3131, was digested to completion by BglII and the enzyme was removed by phenol-chloroform extraction. The plasmid was ethanol-precipitated and dephosphorylated as described by Kendall and Cullum (Gene; 29, 315 (1984)). For ligation, a mixture of partially digested chromosomal *Streptomyces lividans* DNA fragments and dephosphorylated pIJ702 at a ratio of 5:1 were treated with 0.1 unit of T4 DNA ligase overnight at room temperature at a concentration of 37.5 ug/ml.

The *Streptomyces lividans* 1326 was mutated by using N-methyl-N'-nitro-N-nitrosoguanidine (Delic et al., Mutation Res.; 9, 167 (1970)), and a double mutant β-1,4-D-glucan glucanohydrolase (endocellulase)-negative and xylanase-negative was selected. The double mutant was selected on a solid minimal medium containing 1% carboxymethyl-cellulose as main carbon source. Visualization of endocellulase activity was achieved by Congo Red staining according to Teather and Wood, op. cit. The detection of xylanase-negative mutants was carried out in the same manner substituting the carboxymethyl-cellulose by 1% oat spelts xylan. The Congo Red coloration was found to be applicable also for the detection of xylanase activity. In both cases, the absence of decoloration zones was taken as an indication for the absence of enzyme production. The double mutant *Streptomyces lividans* 10-164 was very stable, appeared to give the highest transformation efficiency and was therefore selected as the more preferred host microorganism for the development of the expression system.

Protoplasting and transformation of the double mutant *Streptomyces lividans* 10-164 was performed as described by Chater et al. (Curr. Topics Microbiol. Immunol.; 97, 69 (1982)). Transformed protoplasts were plated on R5 medium supplemented for melanin expression and overlayed with 3 ml of R5 medium containing 0.6% agar at 42° C. Transformants were selected for thiostrepton resistance after 16 hours at 30° C. according to the procedure of Kendall and Cullum, op. cit. (1984). Screening of xylanase-positive clones was done using a minimal medium supplemented with RBB-xylan which was prepared according to Biely et al. (Anal. Biochem.; 144, 142 (1985)). Colonies producing xylanase, hydrolyse this substrate creating clear zones.

Two xylanase-producing clones were selected and designated *Streptomyces lividans* IAF18 and IAF30. Analysis by agarose gel electrophoresis of the plasmidic DNA material found in the *Streptomyces lividans* IAF18 and IAF30 demonstrated that all the plasmids found were larger than pIJ702, i.e. plasmids pIAF18 and pIAF30 had inserts of 5.7 and 6.7 kb, respectively. These hybrid plasmids were used to retransform the double mutant *Streptomyces lividans* 10-164. In all cases, 100% of the transformants were positive for the enzymatic activity previously scored indicating that the presumptive xylanase (xln) gene was plasmid-linked. Restriction mapping of the plasmids pIAF18 and pIAF30 revealed a discrepancy between the two inserts as to the restriction sites. However, Southern blotting, using as a probe the BamHI-SphI restriction fragment internal to the insert pIAF18 showed that about 2 kb of DNA was common to the two inserts.

The expression of the xln gene was studied by submerged cultures of the different clones in TSB (trypticase soy broth) and in xylan medium and compared to the wild-type strains *Streptomyces lividans* 1326 and 3131. The xylan medium, referred to as M13, consists of : xylan (from oat spelts; Sigma Chemical Co., St. Louis, Mo., U.S.A.), 10 g; $(NH_4)_2SO_4$, 1.4 g; $K_2HPO_4$, 2.5 g; $KH_2PO_4$, 1.0 g; yeast extract (Difco), 2 g; proteose peptone (Difco), 1 g; $MgSO_4.7H_2O$, 0.3 g; $CaCl_2.2H_2O$, 0.3 g; Tween 80, 2 ml; and 1 ml of a trace metal solution containing $CoCl_2, 6H_2O$ (200 mg), $FeSO_4.7H_2O$ (500 mg), $MnSO_4, H_2O$ (160 mg) and $ZnSO_4, 7H_2O$ (140 mg), all dissolved in 100 ml of distilled water acidified to pH 3. An incubation temperature of 34° C. was chosen since it afforded a good ratio of growth to xylanase activity (Kluepfel et al., Appl. Microbiol. Biotechnol.; 24, 230 (1986)). The results are shown in Table 1 for 48h and 72h of incubation.

TABLE 1

| The activity is expressed in IU/ml of culture filtrate. | | | |
|---|---|---|---|
| Strain or Clone | Xylanase activity in IU[a] | | |
| | TSB | | Xylan medium |
| | 48 h | 72 h | 48 h | 72 h |
| 1326 | 0 | 0 | 3.1 | 5.8 |
| 3131 | 0 | 0 | 3.7 | 6.3 |
| IAF18 | 4.4 | 4.5 | 293.0 | 380.0 |
| IAF30 | 1.4 | 1.4 | 219.0 | 305.0 |

[a]The assay for xylanase was carried out by incubating 1 ml of enzyme solution appropriately diluted in 0.1M McIlvain buffer pH 6.0 with 1 ml of an aqueous suspension of 1% xylan at 60° C. for 10 min. The reaction was terminated by the addition of 2 ml of dinitro-salicylic acid reagent and by heating for 15 min. in boiling water. The amount of reducing sugars released was determined with D-xylose as standard. The blanks consisted of 1 ml xylan suspension incubated in the same manner to which 2 ml of the dinitro-salicylic acid solution and 1 ml of enzyme were added of the dinitro-salicyclic acid solution and 1 ml of enzyme were added.

The wild-type strain, whether it carried the plasmid pIJ702 or not, produced no enzyme activity when grown in TSB and the levels produced in xylan medium varied between 3 and 6 IU/ml of culture filtrate. The clones IAF18 and IAF30 showed significant activity in TSB(0.9-4.5 IU/ml) even in the absence of any inducer. Clones IAF18 and IAF30 grown in xylan medium produced very high levels of xylanase, e.g. IAF18 reached 380 IU/ml. In the intracellular fraction of all cultures, only trace amounts of xylanase activity were detected, indicating an efficient secretion of the enzyme.

The culture supernatant concentrates of strain *Streptomyces lividans* 3131, and clones IAF18 and IAF30 after induction with xylan were analyzed for secreted xylanase by SDS-9% PAGE after staining with Coomassie Blue. The xylanase-like products of these clones had an estimated $M_r$ of 43,000. This value corresponded exactly to the $M_r$ of the native purified xylanase isolated from *Streptomyces lividans* 1326 (Morosoli et al., 1986) indicating that both the clones had inserts coding at least for the complete structural gene. Furthermore, the identity of these proteins was confirmed immunologically in Western blotting experiments using antixylanase antibodies.

EXAMPLE 2

The genetic stability of *Streptomyces lividans* IAF18 was investigated by testing the enzyme production in TSB and medium M13 containing 1% xylan (hereinabove defined) both in the presence and absence of thiostrepton. In both media, the enzyme levels obtained remained constant for at least ten consecutive transfers and were not affected by the absence of the antibiotic. The multicopy gene effect was observed in TSB where about 2 IU/ml were consistently measured after 24h reaching 10 IU/ml after 48 hours. This level of production remained stable for several days and can be explained by the good stability of the enzyme at 34° C.

The addition of glucose to the medium M13 clearly showed catabolite represssion and enzyme production started when this sugar was exhausted, where as xylose as main carbon source in the same medium yielded extracellular xylanase level of 800 IU/ml as obtained by using xylan alone, as shown in Table 2.

TABLE 2

| carbon source | Activity (IU/ml) | | | | |
|---|---|---|---|---|---|
| | 24 h | 48 h | 72 h | 96 h | 120 h |
| 1% xylan | 143 | 564 | 782 | 957 | 1233 |
| 1% xylan + 1% glucose | 0 | 48 | 462 | 888 | 1085 |
| 1% xylose | 217 | 652 | 672 | 991 | 1216 |

Table 3 shows a comparison of enzyme production between the wild-type strain *Streptomyces lividans* 1326 and the clone *Streptomyces lividans* IAF18 on medium M13 containing 1% and 2% of xylan. The former yielded 28 IU/ml with both concentrations whereas the latter secreted 1300 and 1600 IU/ml of xylanase respectively.

TABLE 3

| Strain and xylan concentration | Activity (IU/ml) | | | | |
|---|---|---|---|---|---|
| | 24 h | 48 h | 72 h | 96 h | 120 h |
| *S. lividans* 1326 | | | | | |
| 1% xylan | 14 | 29 | 30 | 29 | 29 |
| 2% xylan | 8 | 23 | 26 | 27 | 27 |
| *S. lividans* IAF18 | | | | | |
| 1% xylan | 84 | 576 | 898 | 1150 | 1342 |

TABLE 3-continued

| Strain and xylan concentration | Activity (IU/ml) | | | | |
|---|---|---|---|---|---|
| | 24 h | 48 h | 72 h | 96 h | 120 h |
| 2% xylan | 154 | 784 | 1207 | 1408 | 1604 |

EXAMPLE 3

The xylanase production by clone *Streptomyces lividans* IAF18 in Erlenmeyer flasks using medium M13 at 34° C. containing either hay, wheat straw, corn stover, or brewer's spent grains (BSG; O'Keefe Breweries Ltd., Montreal, Quebec) as main carbon source at a concentration of 1% is shown in Table 4. The optimal extracellular xylanase production was obtained after about 72h of incubation with values in the following order: BSG, 274 IU; hay, 217 IU; cornstover, 162 IU and wheat straw, 76 IU per ml of supernatant. In comparison, *Streptomyces lividans* wild-type strain 1326 produced 3.5 IU/ml on BSG.

TABLE 4

| Entry | Time (h) | 1% BSG | 1% Hay | 1% Corn Stover | 1% Wheat Straw |
|---|---|---|---|---|---|
| 1 | 24 | 26.5 | 19 | 10.7 | 5.5 |
| 2 | 48 | 86.6 | 125 | 116 | 72 |
| 3 | 72 | 153 | 217 | 160 | 76 |
| 4 | 96 | 235 | 207 | 162 | 75 |
| 5 | 120 | 274 | 179 | 153 | 66 |
| 6 | 144 | 267 | 182 | 146 | 61 |

EXAMPLE 4

The yeast extract and proteose peptone were eliminated from medium M13 to provide a modified M13. The influence of increasing BSG concentration from 1% to 4% as main carbon source on the xylanase production in the modified medium M13 at 34° C. was examined and the results are listed in Table 5. Optimal enzyme synthesis occurred with 1 and 2% of BSG. Higher concentrations yielded significantly lower levels. In comparison with the values previously found fermenting *Streptomyces lividans* IAF18 on the complete M13 medium, a remarkable increase in xylanase production was observed reaching 800 IU/ml requiring however, a significantly longer fermentation period of 144-168 hours.

TABLE 5

| Entry | Time (h) | 1% BSG | 2% BSG | 3% BSG | 4% BSG |
|---|---|---|---|---|---|
| 1 | 24 | 48.5 | 5.2 | 2.9 | 6.8 |
| 2 | 48 | 216 | 61 | 65 | 140 |
| 3 | 72 | 416 | 182 | 266 | 314 |
| 4 | 96 | 564 | 360 | 376 | 380 |
| 5 | 120 | 703 | 516 | 466 | 418 |
| 6 | 144 | 776 | 709 | 551 | 414 |
| 7 | 168 | 751 | 774 | 578 | 418 |

EXAMPLE 5

The effect of surfactants on xylanase secretion by *Streptomyces lividans* IAF18 in medium M13 with 1% BSG as substrate was examined. Concentrations of 0.2% of the following were used: Tween 80, olive oil (Gattuso Foods Ltd. Montreal, Quebec) or a 1:1 emulsion of both. The results are listed in Table 6. An increase in production of xylanase was obtained with 0.2% olive oil.

TABLE 6

| Entry | Time (h) | Control | Tween 80 | Olive Oil | Emulsion |
|---|---|---|---|---|---|
| 1 | 24 | 77.6 | 109 | 131.8 | 80.2 |
| 2 | 48 | 213.9 | 319.4 | 606.9 | 257 |
| 3 | 72 | 353 | 618 | 1062 | 511 |
| 4 | 96 | 499.5 | 796 | 1237.1 | 734.9 |
| 5 | 120 | 575 | 810 | 1266 | 819 |
| 6 | 144 | 645 | 840 | 342 | 854 |

EXAMPLE 6

The scale-up production of xylanase production from *Streptomyces lividans* IAF18 was carried out in 14 L fermenters. Using the same modified medium M13 containing 1% of BSG and 0.2% olive oil, enzyme levels of 1300 IU/ml were obtained after 120 h of fermentation at 34° C. A further 10% increase in xylanase yields was possible by prolonging the fermentation for another 48 h but cultures are normally harvested after 5 days. The enzyme can be recovered from eh filtrates by simple solvent precipitation with either three volumes of ethanol or two volumes of acetone yielding up to 2 g/L of crude enzyme with a specific activity of about 2000 IU/mg of protein.

EXAMPLE 7

A supernatant of a recombinant *Streptomyces lividans* clone containing the endo-xylanase ($\beta$-1,4-D-xylan xylanohydrolase EC 3.2.1.8) assayed at approximately 1000 IU/ml at a protein concentration of approximately 2 mg/ml (Lowry assay). The supernatant, containing the enzyme was freeze-dried and kept as a powder at −20° C. prior to use. Freeze-drying did not later the enzyme activity.

A Kraft hardwood pulp sample was used for this experiment and showed the following characteristics:
Kappa number: 14.0.
Brightness: 32.7% ISO.
Viscosity: 49.8 cps.

Treated and control samples (50 g O.D. each) were suspended in 1.666 L of 0.1N sodium acetate buffer, pH 5.0 (adjusted with glacial acetic acid), to a consistency of 3%. The treated sample had 2.12 g of freeze-dried xylanase added to it for a final concentration of 127.25 IU/ml. Both samples were incubated at 40° C. for 48 hours at 300 rpm (constant mixing).

Upon completion of the xylanase treatment, the pulp samples were washed with 10 L of distilled water and pressed to about 20% consistency. Brightness, Kappa number and viscosity were measured using "Standard Test Methods" well known in the art. The results are listed in Table 7. Treatment of the pulp with xylanase alone resulted in a significant decrease in the Kappa number (24%), and increases in viscosity (13%) and brightness (25%) as compared to the untreated pulp sample. The control sample, which was subjected to treatment with the buffer only, retained the same starting Kappa number and viscosity as the untreated sample. The brightness of this sample was intermediate between those of the untreated and xylanase treated samples.

TABLE 7

| Effect of Xylanase on Unbleached Pulp Characteristics | | | |
|---|---|---|---|
| TREATMENT | KAPPA | BRIGHTNESS (% ISO) | VISCOSITY (CPS) |
| Untreated | 14.0 | 32.7 | 49.8 |
| Control (Buffer only) | 14.2 | 36.2 | 49.8 |
| Xylanase | 10.7 | 40.8 | 56.4 |
| Control – 1% NaOH Extraction at 21° C. | 14.2 | 35.7 | 48.1 |
| Xylanase – 1% NaOH Extraction at 21° C. | 10.4 | 41.5 | 54.6 |
| Control – 1% NaOH Extraction at 60° C. | 14.0 | 37.0 | 48.4 |
| Xylanase – 1% NaOH Extraction at 60° C. | 10.3 | 45.3 | 51.9 |

Each of the control and xylanase-treated samples were then subjected to a 1% alkali extraction (on pulp), for 1 hour at 21° C. and the results are listed in Table 7. This treatment resulted in small further decreases in the Kappa number and viscosity of the xylanase-treated sample, and resulted in a significant further increase in its brightness. The control sample showed decreases in its brightness and viscosity. In order to drive this extraction further, a second 1% alkali extraction, for 30 minutes at 60° C., was conducted. This resulted in virtually no further change in the Kappa number and only a small further decrease in the viscosity, although the viscosity value is still greater than the starting untreated pulp viscosity. However, the most significant effect was on the brightness of the xylanase-treated pulp sample which increased about 4 points over that of the previous extraction.

Overall, the brightness of the xylanase-treated pulp sample increased about 13 points (about 8 points over the case of the buffer control followed by the alkali extractions), while the Kappa number decreased by about 30%. In this example, the increase in viscosity in the xylanase-treated sample indicates that the enzyme was specifically cleaving the hemicellulose linkages in the pulp without affecting the cellulose linkages.

What is claimed is:

1. A method of hydrolyzing the $\beta$-1,4-D-xylosidic linkage within a lignocellulosic material having xylanase hydrolyzable $\beta$-1,4-D-xylosidic linkages, said method comprising subjecting said material to said hydrolysis by a substantially cellulase-free xylanase obtained from the recombinant microorganism produced by the introduction of a hybrid plasmid into a host microorganism mutant strain of the strain *Streptomyces, lividans* said strain characterized by it having cellulase-negative activity, said hybrid plasmid being constructed by the insertion of the xylanase (xln) gene obtained from a xylanase (xln) gene-containing microorganism of the genus Streptomyces into a vector plasmid obtained from a microorganism of the genus Streptomyces.

2. A method as claimed in claim 1, wherein said host microorganism is a double mutant strain characterized by it having also xylanase-negative activity.

3. A method as claimed in claim 1, wherein said host microorganism is the double mutant strain *Streptomyces lividans* 10-164.

4. A method as claimed in any one of claims 1 to 3, wherein said xylanase (xln) gene is obtained from a xylanase (xln) gene-containing microorganism of the species *Streptomyces lividans*.

5. A method as claimed in any one of claims 1 to 3, wherein said xylanase (xln) gene is obtained from the strain *Streptomyces lividans* 1326.

6. A method as claimed in any one of claims 1 to 3, wherein said vector plasmid is obtained from a microorganism of the species *Streptomyces lividans*.

7. A method as claimed in any one of claims 1 to 3, wherein said vector plasmid is pIJ702.

8. A method as claimed in any one of claims 1 to 3, wherein said xylanase (xln) gene is obtained from a xylanase (xln) gene-containing microorganism of the species *Streptomyces lividans* and said vector plasmid is obtained from a microorganism of the species *Streptomyces lividans*.

9. A method as claimed in any one of claims 1 to 3, wherein said xylanase (xln) gene is obtained form a xylanase (xln) gene-containing microorganism of the species *Streptomyces lividans* and said vector plasmid is pIJ702.

10. A method as claimed in any one of claims 1 to 3, wherein said xylanase (xln) gene is obtained from the strain *Streptomyces lividans* 1326 and said vector plasmid is obtained from a microorganism of the species *Streptomyces lividans*.

11. A method as claimed in any one of claims 1 to 3 wherein said xylanase (xln) gene is obtained from the strain *Streptomyces lividans* 1326 and said vector plasmid is pIJ702.

12. A recombinant microorganism as defined in claim 1, wherein said recombinant microorganism is produced by the introduction of a hybrid plasmid into a host microorganism mutant strain strain *Streptomyces lividans*, said strain characterized by it having cellulase-negative activity, said hybrid plasmid being constructed by the insertion of the xylanase (xln) gene obtained from a xylanase (xln) gene-containing microorganism of the genus Streptomyces into a vector plasmid obtained from a microorganism o the genus Streptomyces.

13. A recombinant microorganism as claimed in claim 12, wherein said host microorganism is a double mutant strain characterized by it having also xylanase-negative activity.

14. A recombinant microorganism as claimed in claim 12, wherein said host microorganism is the double mutant strain *Streptomyces lividans* 10-164.

15. A recombinant microorganism as claimed in any of claims 12-14, wherein said xylanase (xln) gene is obtained from a xylanase (xln) gene-containing microorganism of the species *Streptomyces lividans*.

16. A recombinant microorganism as claimed in any of claims 12-14, wherein said xylanase (xln) gene is obtained from the strain *Streptomyces lividans* 1326.

17. A recombinant microorganism as claimed in any of claims 12-14, wherein said vector plasmid is obtained from a microorganism of the species *Streptomyces lividans*.

18. A recombinant microorganism as claimed in any of claims 12-14, wherein said vector plasmid is pIJ702.

19. A recombinant microorganism as claimed in any one of claims 12-14, wherein said xylanase (xln) gene is obtained form a xylanase (xln) gene-containing microorganism of the species *Streptomyces lividans* and said vector plasmid is obtained from a microorganism of the species *Streptomyces lividans*.

20. A recombinant microorganism as claimed in any of claims 12-14, wherein said xylanase (xln) gene is obtained from a xylanase (xln) gene-containing microorganism of the species *Streptomyces lividans* and said vector plasmid is pIJ702.

21. A recombinant microorganism as claimed in any of claims 12-14, wherein said xylanase (xln) gene is obtained from the strain *Streptomyces lividans* 1326 and said vector plasmid is obtained from a microorganism of the species *Streptomyces lividans*.

22. A recombinant microorganism as claimed in any of claims 12-14, wherein said xylanase (xln) gene is obtained from the strain *Streptomyces lividans* 1326 and said vector plasmid is pIJ702.

23. A host microorganism mutant strain as defined in any one of claims 1 to 3.

24. A hybrid plasmid as defined in claim 1, wherein said xylanase (xln) gene is obtained from the strain *Streptomyces lividans* 1326.

25. A hybrid plasmid as claimed in claim 24, wherein said vector plasmid is obtained from a microorganism of the species *Streptomyces lividans*.

26. A hybrid plasmid as claimed in claim 25, wherein said vector plasmid is pIJ702.

27. A method of bleaching and/or delignification of a lignocellulosic material having xylanase hydrolyzable, B-1,4-D-xylosidic linkages, said method comprising subjecting said material to said hydrolysis by a substantially cellulase-free xylanase obtained from the recombinant microorganism produced by the introduction of a hybrid plasmid into a host microorganism mutant strain Streptomyces lividans, said strain characterized by it having cellulase-negative activity, said hybrid plasmid being constructed by the insertion of the xylanase (xln) gene obtained from a xylanase (xln) gene-containing microorganism of the strain Streptomyces lividans into a vector plasmid obtained from a microorganism of the strain *Streptomyces lividans*.

* * * * *